US010182565B2

(12) United States Patent
Zhang et al.

(10) Patent No.: US 10,182,565 B2
(45) Date of Patent: Jan. 22, 2019

(54) INSECT REPELLENT FIXTURE AND METHOD

(71) Applicant: Sterling International Inc., Spokane, WA (US)

(72) Inventors: Qing-He Zhang, Spokane, WA (US); Rodney G. Schneidmiller, Greenacres, WA (US)

(73) Assignee: Sterling International Inc., Spokane, WA (US)

( * ) Notice: Subject to any disclaimer, the term of this patent is extended or adjusted under 35 U.S.C. 154(b) by 240 days.

(21) Appl. No.: 15/044,753

(22) Filed: Feb. 16, 2016

(65) Prior Publication Data
US 2016/0242405 A1    Aug. 25, 2016

Related U.S. Application Data

(60) Provisional application No. 62/119,025, filed on Feb. 20, 2015.

(51) Int. Cl.
*A01M 29/12* (2011.01)
*A01M 29/00* (2011.01)
(Continued)

(52) U.S. Cl.
CPC ........ *A01M 13/003* (2013.01); *A01M 1/2022* (2013.01); *A01M 1/2027* (2013.01); *A01M 1/2044* (2013.01); *A01M 1/2083* (2013.01); *A01M 29/00* (2013.01); *A01M 29/12* (2013.01); *A01N 25/34* (2013.01); *A01N 61/02* (2013.01); *A01N 65/00* (2013.01); *A01N 65/22* (2013.01); *A01N 65/28* (2013.01); *A01N 65/44* (2013.01)

(58) Field of Classification Search
CPC .... A01M 29/00; A01M 29/12; A01M 1/2022; A01M 1/2027; A01M 1/2044; A01M 1/2055; A01M 1/2061; A01M 1/2083; A61L 9/03; A61L 9/037; A61L 9/12; A61L 9/127
USPC ..... 43/132.1, 124, 131, 113; 239/34, 37–44, 239/54–57; 392/96
See application file for complete search history.

(56) References Cited

U.S. PATENT DOCUMENTS

| | | | | |
|---|---|---|---|---|
| 439,317 A | * | 10/1890 | Allen | ........................ A61L 9/12 239/55 |
| 845,174 A | * | 2/1907 | Hillyard | .................... A61L 9/12 239/51.5 |

(Continued)

FOREIGN PATENT DOCUMENTS

| | | | | |
|---|---|---|---|---|
| DE | 2551185 A1 | * | 5/1977 | ............ A01M 29/12 |
| EP | 1776862 A1 | * | 4/2007 | .......... A01M 1/2055 |

(Continued)

*Primary Examiner* — Darren W Ark
(74) *Attorney, Agent, or Firm* — Christensen O'Connor Johnson Kindness, PLLC; Ryan Dodge

(57) ABSTRACT

A fixture (100) for gradually releasing a spatially effective semiochemical, for example a repellant. The fixture includes a slotted tube (140), that may be formed for example, from a porous material, a peripheral tube (102) having a plurality of apertures and disposed outward from the slotted tube, a base (110) that engages the slotted tube and the outer tube, a funnel member (160) that engages a top end of the slotted tube and the peripheral tube, and a cap (130). In an embodiment the base includes a lighting element (150).

11 Claims, 4 Drawing Sheets

(51) Int. Cl.
*A01M 1/20* (2006.01)
*A01M 13/00* (2006.01)
*A01N 61/02* (2006.01)
*A01N 25/34* (2006.01)
*A01N 65/00* (2009.01)
*A01N 65/22* (2009.01)
*A01N 65/28* (2009.01)
*A01N 65/44* (2009.01)

(56) References Cited

U.S. PATENT DOCUMENTS

| | | | | |
|---|---|---|---|---|
| 926,961 A * | 7/1909 | Raforth | A01G 27/001 | 239/51 |
| 984,352 A * | 2/1911 | Costello | A01M 1/2055 | 206/0.5 |
| 1,013,514 A * | 1/1912 | Rand | | 43/131 |
| 1,071,326 A * | 8/1913 | Maas | A61L 9/127 | 237/78 R |
| 1,236,245 A * | 8/1917 | Abadie | | 43/131 |
| 1,477,273 A * | 12/1923 | Liss | A01M 1/2044 | 43/131 |
| 1,732,028 A * | 10/1929 | Reiner | A01M 1/2044 | 119/654 |
| 1,769,409 A * | 7/1930 | Armstrong | A01M 1/2055 | 239/56 |
| 1,823,892 A * | 9/1931 | Galbraith | A01M 1/2016 | 43/112 |
| 2,086,046 A * | 7/1937 | Preston | A01M 1/2055 | 424/84 |
| 2,247,600 A * | 7/1941 | Brennan | A01M 1/2055 | 239/57 |
| 2,438,129 A * | 3/1948 | Rich | A24F 25/02 | 222/544 |
| 2,481,296 A * | 9/1949 | Dupuy | A61L 9/127 | 239/42 |
| 2,559,126 A * | 7/1951 | Lien | | 239/44 |
| 2,606,065 A * | 8/1952 | Logan | A01M 29/12 | 239/53 |
| 2,690,030 A * | 9/1954 | Thompson | A01M 1/02 | 239/56 |
| 2,698,767 A * | 1/1955 | Hartmann | A61L 9/12 | 239/44 |
| 2,708,595 A * | 5/1955 | Ludwig | B65F 7/00 | 239/57 |
| 2,723,158 A * | 11/1955 | Molina | A61L 9/12 | 239/44 |
| 2,738,225 A * | 3/1956 | Meek | A61L 9/12 | 239/55 |
| 2,765,194 A * | 10/1956 | Will | A01M 1/2055 | 239/59 |
| 3,017,117 A * | 1/1962 | Klingler | A47K 10/32 | 239/52 |
| 3,108,391 A * | 10/1963 | Sipos | A01M 1/04 | 43/113 |
| 3,204,871 A * | 9/1965 | Callander | A01M 1/2044 | 222/187 |
| 3,421,841 A * | 1/1969 | Wittwer | A01M 1/2077 | 392/392 |
| 3,515,302 A * | 6/1970 | Curran | A61L 9/12 | 220/4.01 |
| 3,565,339 A * | 2/1971 | Curran | A61L 9/12 | 239/60 |
| 3,727,840 A * | 4/1973 | Nigro | A61L 9/127 | 239/43 |
| 3,807,082 A * | 4/1974 | Hautmann | A61L 9/12 | 43/125 |
| 3,817,371 A * | 6/1974 | Gatter | A01M 1/2055 | 206/0.5 |
| 3,837,574 A * | 9/1974 | Curran | A61L 9/12 | 206/0.5 |
| 3,896,995 A * | 7/1975 | Lelicoff | A01M 1/2044 | 239/36 |
| 3,959,642 A * | 5/1976 | Turro | A61L 9/03 | 362/92 |
| 4,065,872 A * | 1/1978 | Patton | A01M 1/2011 | 43/131 |
| 4,165,835 A * | 8/1979 | Dearling | A61L 9/12 | 239/45 |
| 4,166,087 A * | 8/1979 | Cline | A61L 9/122 | 239/56 |
| 4,220,281 A * | 9/1980 | Martens, III | A61B 5/0816 | 239/57 |
| 4,228,124 A * | 10/1980 | Kashihara | A01M 1/2072 | 392/386 |
| 4,247,042 A * | 1/1981 | Schimanski | A01M 1/2044 | 239/43 |
| 4,323,193 A * | 4/1982 | Compton | A61L 9/127 | 239/44 |
| 4,523,870 A * | 6/1985 | Spector | A61L 9/12 | 239/55 |
| 4,526,320 A * | 7/1985 | von Philipp | A01M 1/2044 | 239/34 |
| 4,549,693 A * | 10/1985 | Barlics | A61L 9/12 | 206/0.5 |
| 4,630,775 A * | 12/1986 | Mandon | A01M 1/2044 | 239/56 |
| 4,654,998 A * | 4/1987 | Clay | A01M 1/145 | 43/113 |
| 4,662,103 A * | 5/1987 | Cheng | A01M 1/2044 | 43/131 |
| 4,671,010 A * | 6/1987 | Conlee | A01M 1/02 | 43/114 |
| 4,782,622 A * | 11/1988 | Roberts | A01M 25/00 | 114/221 R |
| 4,802,303 A * | 2/1989 | Floyd, III | A01M 1/02 | 43/114 |
| 4,804,142 A * | 2/1989 | Riley | A01M 29/12 | 239/56 |
| 4,908,977 A * | 3/1990 | Foster | A01M 1/02 | 43/107 |
| 4,917,301 A * | 4/1990 | Munteanu | A61L 9/01 | 239/43 |
| 5,033,229 A * | 7/1991 | Demarest | A01M 1/2011 | 43/124 |
| 5,033,674 A * | 7/1991 | Smith | A61L 9/12 | 239/34 |
| 5,064,624 A * | 11/1991 | King | A61L 9/12 | 137/268 |
| 5,150,541 A * | 9/1992 | Foster | A01M 1/02 | 43/131 |
| 5,203,816 A * | 4/1993 | Townsend | A01M 1/145 | 43/113 |
| 5,359,808 A * | 11/1994 | Fitsakis | A01M 1/2016 | 43/131 |
| 5,379,545 A * | 1/1995 | Gall | A01M 29/12 | 239/57 |
| 5,603,455 A * | 2/1997 | Lin | A61L 9/12 | 239/326 |
| 5,651,942 A * | 7/1997 | Christensen | A61L 9/03 | 422/125 |
| 5,744,106 A * | 4/1998 | Eagle | A01M 1/2088 | 239/129 |
| 5,749,168 A * | 5/1998 | Chrysanthis | A01M 1/02 | 43/114 |
| 5,943,815 A * | 8/1999 | Paganessi | A01M 1/023 | 43/107 |
| 5,943,816 A * | 8/1999 | Hyatt | A01M 1/2005 | 239/34 |
| 6,016,625 A * | 1/2000 | Bishoff | A01M 1/026 | 43/107 |
| 6,031,967 A * | 2/2000 | Flashinski | A01M 1/2077 | 239/55 |
| 6,340,120 B1 * | 1/2002 | Seymour | A01M 1/2027 | 239/34 |
| 6,467,216 B2 * | 10/2002 | McManus | A01M 1/2005 | 43/131 |
| 6,553,712 B1 * | 4/2003 | Majerowski | A01M 1/2011 | 239/44 |

(56) References Cited

U.S. PATENT DOCUMENTS

| | | | | |
|---|---|---|---|---|
| 6,708,445 B1 * | 3/2004 | Israely | A01M 1/02 |
| | | | 43/131 |
| 6,854,208 B1 * | 2/2005 | Chuang | A01M 1/2027 |
| | | | 261/84 |
| 7,147,171 B2 * | 12/2006 | Harada | A61L 9/12 |
| | | | 239/36 |
| 7,168,630 B1 * | 1/2007 | Ketcha | A01M 1/205 |
| | | | 239/128 |
| 7,325,358 B1 * | 2/2008 | Chalupsky | A01M 29/12 |
| | | | 239/34 |
| 7,380,370 B2 * | 6/2008 | Livingston | A01M 29/12 |
| | | | 239/47 |
| 7,419,102 B2 * | 9/2008 | Harris, Jr. | A01M 1/2044 |
| | | | 239/145 |
| 7,712,249 B1 * | 5/2010 | Modlin | A01M 1/205 |
| | | | 239/102.2 |
| 7,988,984 B2 * | 8/2011 | Hockaday | A01M 1/02 |
| | | | 119/654 |
| 8,119,072 B2 * | 2/2012 | D'Amico | C11B 5/0078 |
| | | | 422/126 |
| 8,281,514 B2 * | 10/2012 | Fleming | A01M 1/04 |
| | | | 239/34 |
| 8,296,993 B2 * | 10/2012 | Modlin | A01M 29/12 |
| | | | 239/102.2 |
| 8,430,336 B2 * | 4/2013 | Pisklak | A61L 9/127 |
| | | | 222/187 |
| 8,480,248 B2 * | 7/2013 | Demarest | H05B 33/0827 |
| | | | 362/101 |
| 8,746,505 B2 * | 6/2014 | Demarest | A01M 1/2033 |
| | | | 222/113 |
| 9,155,813 B2 * | 10/2015 | Westphal | A61L 9/122 |
| 9,185,898 B2 * | 11/2015 | McIntyre | A01M 1/2055 |
| 9,271,486 B2 * | 3/2016 | Messina | A01N 25/00 |
| 9,327,044 B2 * | 5/2016 | Olchovy | A61L 9/12 |
| 9,474,821 B2 * | 10/2016 | Lesniak | A61L 9/12 |
| 9,751,660 B2 * | 9/2017 | Jasin | B65D 21/086 |
| 9,756,857 B2 * | 9/2017 | Jones | A01N 41/04 |
| 2006/0102737 A1 * | 5/2006 | Harmon | A01M 1/2055 |
| | | | 239/6 |
| 2008/0066372 A1 * | 3/2008 | Fleming | A01M 1/04 |
| | | | 43/113 |
| 2008/0311008 A1 * | 12/2008 | Tranzeat | A01M 1/2033 |
| | | | 422/124 |
| 2010/0284168 A1 * | 11/2010 | Walter | A01M 1/205 |
| | | | 362/96 |
| 2013/0156839 A1 * | 6/2013 | Messina | A01N 37/06 |
| | | | 424/410 |
| 2013/0298446 A1 * | 11/2013 | Rubel | A01M 1/2055 |
| | | | 43/132.1 |
| 2015/0144713 A1 * | 5/2015 | Formico | A01M 29/12 |
| | | | 239/276 |
| 2015/0290351 A1 * | 10/2015 | Slade | A01M 29/12 |
| | | | 239/44 |
| 2016/0144064 A1 * | 5/2016 | Santini | A61L 9/127 |
| | | | 239/6 |

FOREIGN PATENT DOCUMENTS

| | | | | |
|---|---|---|---|---|
| FR | 2663507 A1 * | 12/1991 | | A01M 1/2055 |
| GB | 2269103 A * | 2/1994 | | A01M 1/2055 |
| GB | 2496741 A * | 5/2013 | | A01N 65/00 |
| JP | 2007007367 A * | 1/2007 | | |
| JP | 5249658 B2 * | 7/2013 | | |
| JP | 5252659 B2 * | 7/2013 | | |
| JP | 5628009 B2 * | 11/2014 | | |
| WO | WO-9830124 A1 * | 7/1998 | | A01M 29/12 |

* cited by examiner

INSECT REPELLENT FIXTURE AND METHOD

CROSS-REFERENCE TO RELATED APPLICATION

This application claims the benefit of U.S. patent application Ser. No. 62/119,025, filed Feb. 20, 2015, the disclosure of which is incorporated by reference herein in its entirety.

BACKGROUND

Repellents provide excellent protection against vector-borne diseases, including malaria, dengue fever, Zika fever, and leishmaniasis. In addition to the well-known topical repellents (e.g., DEET), recent attention has been paid toward the discovery of active spatial repellents. A spatial repellent is a repellent that is effective at a distance from the point of application. The spatial repellent includes an inhibiting compound that, when dispensed into the atmosphere of a three dimensional environmental space, inhibits the ability of mosquitoes to locate and track a target, such as humans or livestock. Many natural essential oils can be effective as spatial repellent against mosquitoes, biting flies, and stinging insects. Without wishing to be bound by theory, it is believed that repellency is positively correlated to the overall release rate of the active spatial repellent compounds. One of the major challenges for insect repellent product development is to design a release device that could maximize the release rates of the active repellent compounds for optimal repellency.

Accordingly, there is a need for release devices that can increase release rates of active repellent compounds. The present disclosure seeks to fulfill these needs and provides related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a spatial repellent fixture including (i) a slotted tube that is configured to adsorb a liquid repellent such that volatiles of the adsorbed liquid repellent are gradually released, wherein the tube includes a plurality of elongate slots; (ii) a peripheral tube having a plurality of apertures therethrough, wherein the peripheral tube is disposed radially outwardly from the slotted tube; (iii) a base that engages a bottom end of the slotted tube and a bottom end of the peripheral tube; and (iv) a cap assembly that engages a top end of the slotted tube and a top end of the peripheral tube.

In another aspect, the present disclosure features a spatial repellent system including a fixture including (i) a slotted tube having a plurality of elongate slots; (ii) a peripheral tube having a plurality of apertures therethrough, wherein the peripheral tube is disposed radially outwardly from the slotted tube; (iii) a base that engages a bottom end of the slotted tube and a bottom end of the peripheral tube; and (iv) a cap assembly that engages a top end of the slotted tube and a top end of the peripheral tube; and a liquid repellent configured to be adsorbed onto the slotted tube such that volatiles of the adsorbed liquid repellent are gradually released from the slotted tube.

In some embodiments, the spatial repellent systems of the present disclosure repel stinging insects, biting insects, or both stinging and biting insects. For example, the spatial repellent system can repel mosquitoes, paper wasps, hornets, yellow jackets, cockroaches, ants, or any combination thereof. As another example, the spatial repellent system can repel mosquitoes, paper wasps, hornets, yellow jackets, or any combination thereof.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
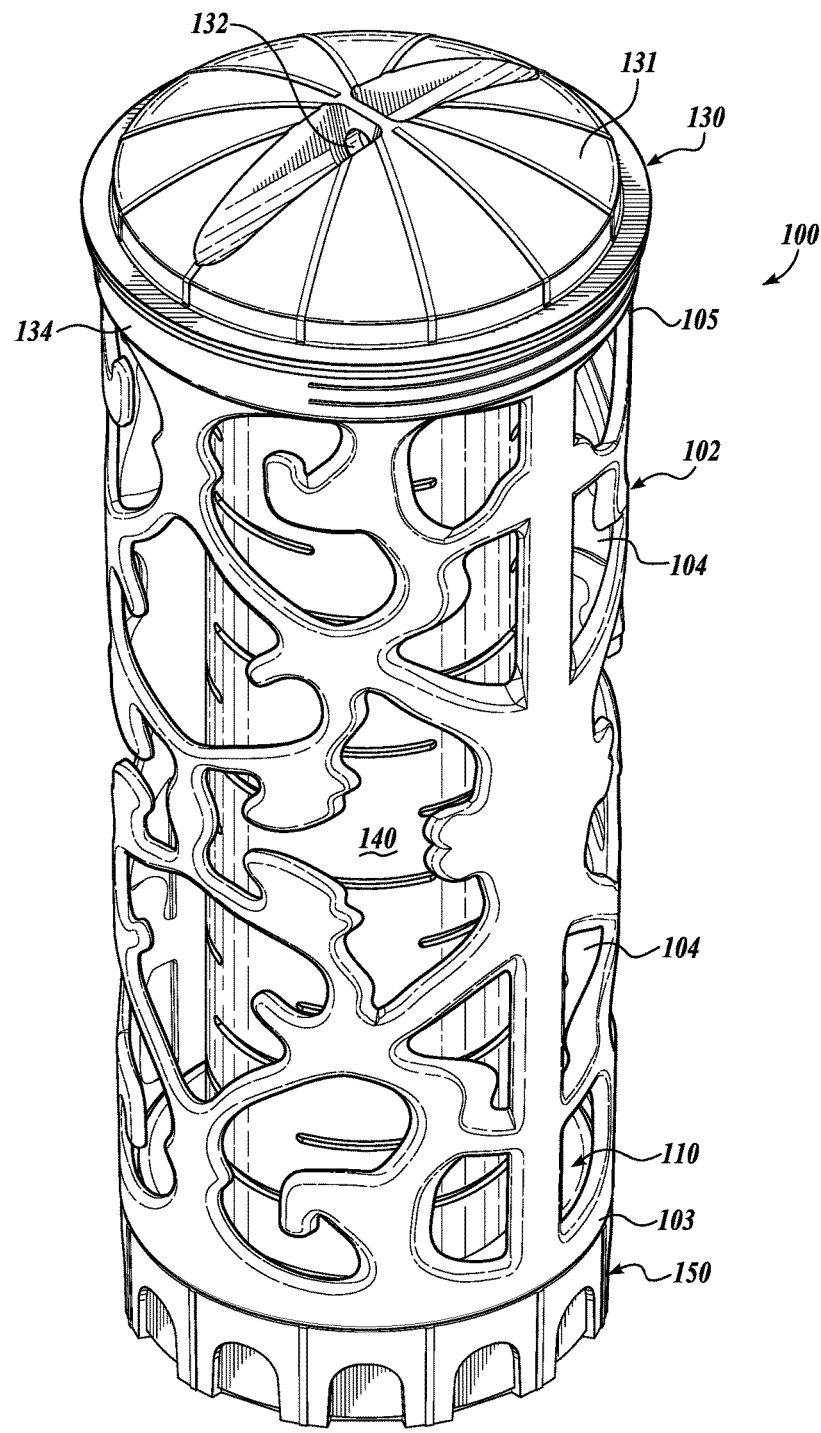
FIG. 1 is an upper perspective view of a repellent fixture in accordance with the present disclosure.

Disclosed herein are porous plastic-based repellent fixtures that release volatile spatial repellent formulations into the air at a steady and optimal rate to achieve a desired repellency effect. A repellent fixture 100 in accordance with the present disclosure is shown in FIG. 1. In this embodiment the fixture 100 comprises an outer tubular member forming a peripheral wall 102. The peripheral wall 102 includes a plurality of large apertures 104 therethrough that allow and encourage air flow through the fixture 100. In the current embodiment the large apertures 104 provide an aesthetically pleasing decorative appearance to the fixture 100.

Figure 2:
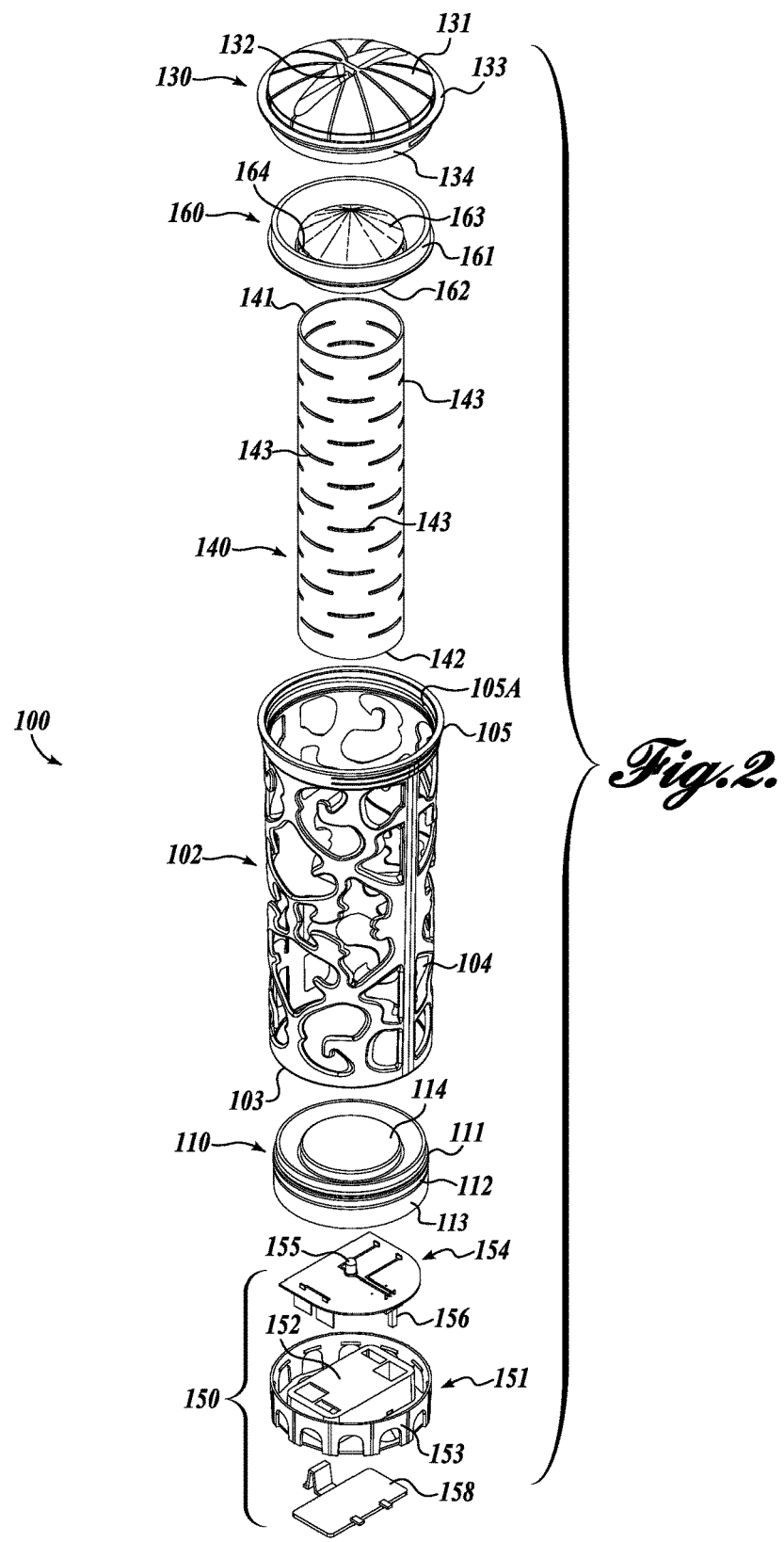
FIG. 2 is an upper exploded view of the repellent fixture shown in FIG. 1.
Figure 3:
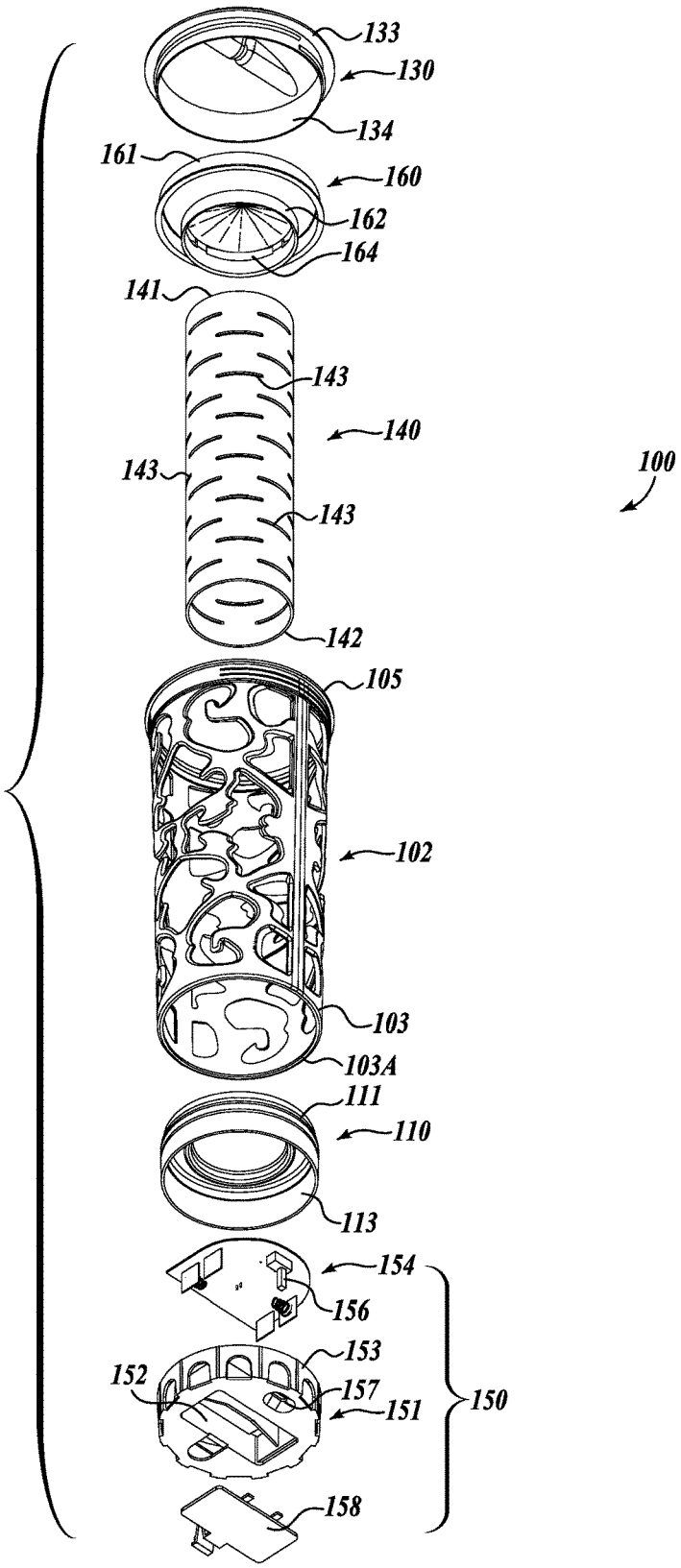
FIG. 3 is a lower perspective view of the repellent fixture shown in FIG. 1.

Refer now also to FIG. 2, which shows an exploded upper-front view of the fixture 100 and to FIG. 3, which shows an exploded lower-front view of the fixture 100. The peripheral wall 102 includes an open lower end 103, with an inner bead or flange 103A and an open upper end 105 with an inwardly threaded portion 105A. The lower end 103 of the peripheral wall 102 is closed by a base 110. The base 110 has an upper cylindrical portion that includes an annular protrusion 111 sized to engage the flange 103A of the peripheral wall 102, and a flange portion 112 that supports the peripheral wall 102. A lower wall portion 113 extends downwardly from the flange portion 112. The upper face of the base 110 defines a center post 114 that is sized and configured to slidably receive and support an inner slotted tube 140, as described in more detail below.

Optionally, the base 110 may further comprise a light assembly 150. In the current embodiment the light assembly 150 includes a body portion 151 that includes a battery compartment 152 and cover 158 configured to receive one or more conventional batteries (not shown), and a decorative surrounding wall 153. In the current embodiment the surrounding wall 153 is open upwardly, and is sized and configured to receive the lower wall portion 113 of the base 110. A circuit board 154 is supported on the body portion 151 above the battery compartment 152 and includes a light element 155, for example a light emitting diode. A switch 156 extends through an aperture 157 in the body portion 151, and is operable to permit the user to activate the light element 155. If the optional light assembly 150 is included, preferably the base 110, or a selected portion of the base 110, is formed from a transparent or translucent material.

The upper end 105 of the peripheral wall 102 is closed by a threaded cap 130. The threaded cap 130 in this embodiment includes an upper dome portion 131 that preferably defines an aperture 132 to facilitate placement of the repellent fixture 100, for example to allow the fixture 100 to be suspended from a branch, eave, or the like.

An outwardly-extending flange 133 is sized to abut the upper end 105 of the peripheral wall 102. An annular wall portion 134 is sized to be threaded onto the upper end 105 of the peripheral wall 102.

Figure 4A:
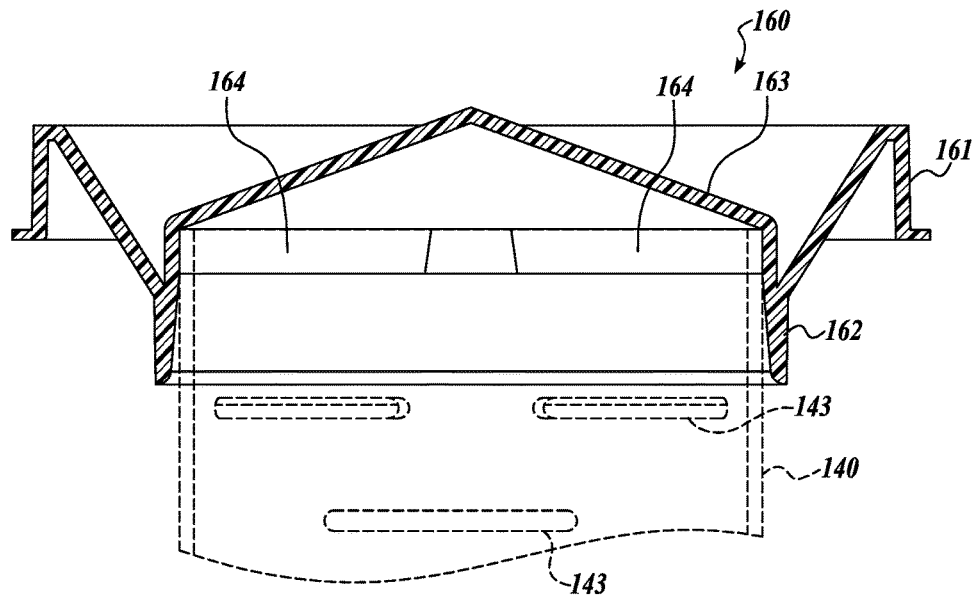
FIG. 4A is a cross sectional view of the funnel member for the repellent fixture shown in FIG. 1.

Refer now also to FIG. 4A, which shows a funnel member 160 in cross section, with the slotted tube 140 partially shown in phantom. The funnel member 160 has a lower portion that receives an upper end of the slotted tube 140 and an upper portion that is received into the threaded cap 130. The funnel member 160 includes an outer wall portion 161 that is sized and configured to engage the annular wall portion 134 of the cap 130 (not shown in FIG. 4A), and an inner wall portion 162 having an angled segment that extends downward from the top end of the outer wall portion 161 and a second segment that engages the slotted tube 140. A sloped upper wall 163, preferably a generally conical wall, extends over the inner wall portion 162. A plurality of narrow slots between the upper wall 163 and the cylindrical portion of the inner wall 162 define ports 164 in the top of the funnel member 160, with sloping walls 162 and 163 on either side of the ports 164. It will be appreciated that the sloping wall 162 will funnel liquid material poured onto the top of the funnel member 160 (for example, a liquid repellent), through the ports 164 and onto the slotted tube 140. In this embodiment the deposited liquid material flows onto an inner surface of the slotted tube 140, and as it travels down by gravity portions of the liquid will flow through the slots 143 onto an outer surface of the slotted tube 140.

Figure 4B:
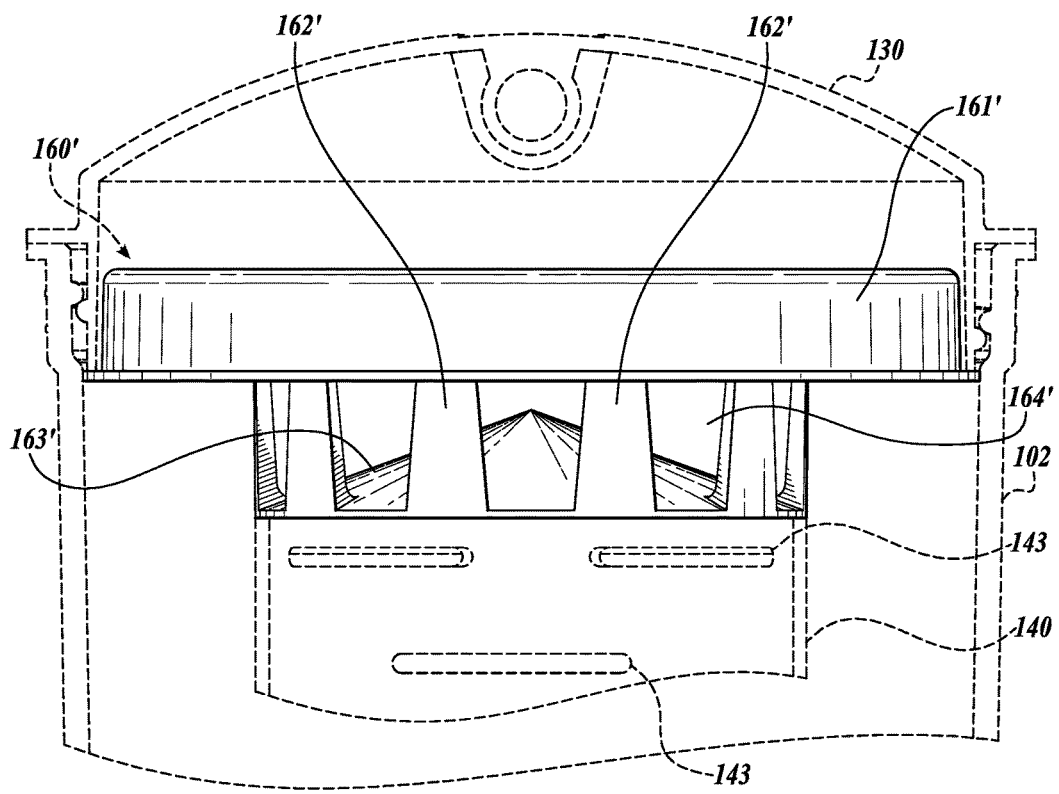
FIG. 4B is a front view of a second embodiment of a funnel member for the repellent fixture shown in FIG. 1.

A second embodiment of a suitable funnel member 160' is shown in FIG. 4B. In this embodiment the funnel member 160' includes an annular portion 161' that is sized to be received into the threaded cap 130 (not shown) and a plurality of posts 162' that extend down and support a sloped surface 163', preferably a generally conical wall, that is located on top of the slotted tube 140. The open areas between the posts 162' define ports 164'. It will be appreciated that the sloped surface 163' will funnel liquid material poured onto the top of the funnel member 160' (for example a liquid repellent), through the ports 164' and onto the slotted tube 140. In this embodiment the deposited liquid material flows onto an outer surface of the slotted tube 140, and as it travels down by gravity portions of the liquid will flow further along the outer surface of the slotted tube 140.

The inner slotted tube 140 in the present embodiment is a right circular tube, sized and configured to slidably engage the center post 114 in the base 110 and the cylindrical portion of the inner wall 162 or the outer wall 161 in the funnel member 160. Therefore, the slotted tube 140 is positioned within the peripheral wall 102 by the base 110 and the funnel member 160. In the present embodiment the slotted tube 140 is coaxially arranged with the peripheral wall 102. However, it will be readily apparent to persons of skill in the art that the slotted tube 140 may be alternatively shaped. For example, the slotted tube may be a non-circular tube, with corresponding changes to the post 114 and the inner annular wall 135. Similarly, the slotted tube 140 may be configured to be disposed off-center, or at an angle with the peripheral wall 102. It is also contemplated that the diameter of the slotted tube 140 may vary along its length, for example tapering from the top to the bottom, having a maximum diameter near the center, or having multiple bulges along its length.

The slotted tube 140 in a current embodiment is formed as a porous tube, and may be formed, for example from a porous polypropylene or polyethylene. In a current embodiment the porous material has a pore size of between 10-150 microns, and a thickness between 1-10 mm. The slotted tube 140 in the current embodiment has a diameter or maximum transverse dimension between 10-300 mm, and a length between 50-400 mm. As discussed below, the porous plastic tube 140 is loaded with a liquid insect repellent that is configured to evaporate or volatilize over time. The volatilized repellent will escape gradually, forming a plume to provide an extended period of protection from the insect species targeted by the repellent. In one embodiment the slotted tube has a cross-section that is star-shaped cross-section to increase the surface area of the slotted tube, e.g., to achieve a desired volatilization rate for the liquid repellent, as well as to increase the repellent-storage capacity of the slotted tube 140. Similarly, it is contemplated that the slotted tube 140 may be formed with inwardly-extending and/or outwardly-extending fins (not shown).

The slotted tube 140 includes a plurality of circumferential, generally horizontal slots 143 therethrough. In the present embodiment the slots 143 are arranged in eight overlapping columns along the length of the slotted tube 140. The slots 143 aid in preventing or slowing the downward migration of liquid repellent adsorbed into the porous plastic tube 140. Therefore, the upper portion of the slotted tube 140 is less prone to dry out before the lower portion of the slotted tube 140. In the current embodiment the slots 143 are oriented horizontally, approximately perpendicular to the axis of the slotted tube 140. In an embodiment the slots 143 are formed by a process that partially or fully seals the micro-pores in the tube in the edge of the slots 143, to aid in preventing downward migration of the repellent.

Of course other shapes and arrangements of the slots are possible and contemplated by the present disclosure. For example, the slots may be formed with a concave upper edge, such that liquid repellent is less likely to flow around the slots. More or fewer columns of slots may be provided. For example, the slots may be arranged in two or more overlapping or staggered columns. In some embodiments, the slots 140 account for 5% or more (e.g., 10% or more, or 15% or more) and/or 20% or less (e.g., 15% or less, or 10% or less) of the total tube surface area. In the currently preferred embodiment the slots 140 account for 5% to 20% of the total tube surface area.

The slots 143 also provide for air flow through the slotted tube 140. Therefore volatiles that are released from the inner surface of the tube 140 will more readily escape to contribute to the formation of the repellent plume. This arrangement will allow the density of volatiles to periodically increase inside the slotted tube 140 until a breeze urges more of the interior volatiles to escape, producing a desirable wafting effect of increasing plume density.

As noted above, the fixture may include a light assembly 150 that is configured to direct light through the base 110 and into the slotted tube 140. The light assembly 150 may improve the aesthetics of the fixture 100. In addition, the light element 155 may generate heat to encourage convective flow within the slotted tube 140, to improve the release rate of the volatiles. It is contemplated that the light element 155 may be replaced by, or supplemented with, a low-power, low-volume fan (not shown) configured to direct air upwardly through the slotted tube.

In use, the slotted tube is loaded with a liquid repellent. The liquid repellent may be loaded onto or into the slotted tube 140 in a number of different ways. In one embodiment the slotted tube is immersed in a reservoir of liquid repellent for a period of time, optionally in a pressurized enclosure, such that the liquid repellent is urged into the porous plastic substrate. In other embodiments the liquid repellent is sprayed onto, painted onto, or flowed over the slotted tube 140, such that it adheres to the surface. In yet another embodiment the slotted tube 140 is packaged in a leak-resistant packaging that also contains a quantity of liquid repellent, such that the liquid repellent is adsorbed into the substrate over a longer period of time.

In a current embodiment it is contemplated that the slotted tube 140 is periodically replenished with liquid repellent by removing the cap 130 and pouring a quantity of liquid repellent onto the funnel member 160. The viscous liquid repellent will gradually flow by gravity through the inlets 164 and along the slotted tube 140. The slots 143 in the slotted tube 140 will reduce the downward migration effect of the liquid repellent after loading by creating many partially separated disk regions along the length of the tube 140. The slots 143 may also reduce the required repellent loading quantity, and increase the release/loading ratio (by an estimated 30-70%). The slots 143 will also increase the overall release rate by an estimated 20-50%, depending the number and area of the slots by improving the air-flow through the slotted tube 140.

Although the fixture 100 is disclosed with regard to a spatial repellent functionality, it will be appreciated that it is sometimes desirable to attract insects into a particular area, for example honeybees or other pollinators. The fixture 100 described above is also effective to provide a spatial attractant, with the use of a suitable semiochemical formulation, as are known in the art.

The liquid repellent that is loaded into the slotted tube can include a combination of essential oils. In some embodiments, the liquid repellent includes (consists essentially of, or consists of) clove oil, lemongrass oil, peppermint oil, cinnamon oil, geranium oil, rosemary oil, and/or citronella oil. For example, a general liquid repellent can include, consists essentially of, or consists of clove oil, lemongrass oil, peppermint oil, and cinnamon oil. In some embodiments, a liquid repellent includes, consists essentially of, or consists of clove oil, lemongrass oil, peppermint oil, and cinnamon oil, and can be used to repel mosquitoes. In some embodiments, a liquid repellent includes, consists essentially of, or consists of clove oil, lemongrass oil, geranium oil, and rosemary oil, and can be used to repel paper wasps, hornets, yellowjackets, and other stinging or biting insects. In certain embodiments, a liquid repellent includes, consists essentially of, or consists of lemongrass oil, peppermint oil, geranium oil, rosemary oil, and citronella oil, and can be used to repel cockroaches or ants.

The liquid repellent can include, consists essentially of, or consists of the essential oils in any proportion. For example, a general liquid insect repellent can include, consists essentially of, or consists of clove oil, lemongrass oil, peppermint oil, and cinnamon oil in a weight ratio of 1:1:0.25:0.1, respectively. In some embodiments, the general insect liquid repellent includes, consists essentially of, or consists of from about 30% (e.g., from about 35%, or from about 40%) to about 50% (e.g., to about 45%, to about 40%, or to about 35%) (e.g., 42.5%) by weight clove oil; from about 30% (e.g., from about 35%, or from about 40%) to about 50% (e.g., to about 45%, to about 40%, or to about 35%) (e.g., 42.5%) by weight by weight lemongrass oil; from about 5% (e.g., from about 8%, from about 10%) to about 15% (e.g., to about 12%, or to about 11%) (e.g., 10.6%) by weight peppermint oil, and/or from about 1% (e.g., from about 3%, or from about 5%) to about 10% (e.g., to about 5%, or to about 3%) (e.g., 4.2%) by weight cinnamon oil, based on the total weight of the essential oil combination, and so long as the total % by weight of the essential oils adds to 100% by weight.

As another example, the clove oil, lemongrass oil, peppermint oil, and cinnamon oil in a liquid repellent that can be used to repel mosquitoes can be present in a ratio of 1:1:1:0.1, respectively. In some embodiments, the liquid repellent includes, consists essentially of, or consists of from about 20% (e.g., from about 25%, from about 30%, or from about 35%) to about 40% (e.g., to about 35%, to about 30%, or to about 25%) (e.g., 32.3%) by weight clove oil; from about 20% (e.g., from about 25%, from about 30%, or from about 35%) to about 40% (e.g., to about 35%, to about 30%, or to about 25%) (e.g., 32.3%) by weight lemongrass oil, from about 20% (e.g., from about 25%, from about 30%, or from about 35%) to about 40% (e.g., to about 35%, to about 30%, or to about 25%) (e.g., 32.3%) by weight peppermint oil, and from 2% (e.g., from about 2.5%, from about 3%, or from about 3.5%) to 4% (e.g., to about 3.5%, to about 3%, or to about 2.5%) (e.g., 3%) by weight cinnamon oil, based on the total weight of the essential oil combination, and so long as the total % by weight of the essential oils adds to 100% by weight.

As yet another example, the clove oil, lemongrass oil, geranium oil, and rosemary oil in a wasp, hornet, yellowjacket wasp, and other biting insect liquid repellent can be present in a ratio of 199:199:1:1, respectively. In some embodiments, the liquid repellent includes, consists essentially of, or consists of from about 40% (e.g., from about 45%, from about 50%, or from about 55%) to about 60% (e.g., to about 55%, to about 50%, or to about 45%) (e.g., 49.75%) by weight clove oil; from about 40% (e.g., from about 45%, from about 50%, or from about 55%) to about 60% (e.g., to about 55%, to about 50%, or to about 45%) (e.g., 49.75%) by weight lemongrass oil, from about 0.1% (from about 0.2%, or from about 0.3%) to about 0.4% (e.g., to about 0.3%, or to about 0.2%) (e.g., 0.25%) by weight geranium oil, and from 0.1% (from about 0.2%, or from about 0.3%) to about 0.4% (e.g., to about 0.3%, or to about 0.2%) (e.g., 0.25%) by weight rosemary oil, based on the total weight of the essential oil combination, and so long as the total % by weight of the essential oils adds to 100% by weight.

As yet another example, the lemongrass oil, peppermint oil, geranium oil, rosemary oil, and citronella oil in a cockroach liquid repellent can be present in an amount of 5:3:1:0.5:0.5, respectively. In some embodiments, the liquid repellent includes, consists essentially of, or consists of from about 40% (e.g., from about 45%, from about 50%, or from about 55%) to about 60% (e.g., to about 55%, to about 50%, or to about 45%) (e.g., 50%) by weight lemongrass oil, from about 20% (e.g., from about 25%, from about 30%, or from about 35%) to about 40% (e.g., to about 35%, to about 30%, or to about 25%) (e.g., 30%) by weight peppermint oil, from about 5% (e.g., from about 7%, from about 10%, or from about 12%) to about 15% (e.g., to about 12%, to about 10%, or to about 7%) (e.g., 10%) by weight geranium oil, from about 1% (e.g., from about 3%, from about 5%, or from about 7%) to about 10% (e.g., to about 7%, to about 5%, or to about 3%) (e.g., 5%) by weight rosemary oil, and from about 1% (e.g., from about 3%, from about 5%, or from about 7%) to about 10% (e.g., to about 7%, to about 5%, or to about 3%) (e.g., 5% by weight) citronella oil, based on the total weight of the essential oil combination, and so long as the total % by weight of the essential oils adds to 100% by weight.

The combination of essential oils can be a neat liquid repellent composition, where the liquid repellent composition does not include carriers. In some embodiments, the combination of essential oils can include additional carriers, antioxidants, and/or preservatives.

Exemplary carriers for liquid repellent include oils; polymers (e.g., polyethylene glycol, polymethacrylates, ethylene-vinyl acetate copolymers, poly(acrylic acid), polyolefins (e.g., polypropylene), poly(urethane), silicones, lactic and glycolic acid-based polymers, and copolymers thereof).

Exemplary oils to use with liquid repellent include, but are not limited to, oils derived from plants such as vegetable oils and nut oils. These are widely available and cost effective. Formulations can include oils such as canola oil, cottonseed oil, palm oil, safflower oil, soybean oil, corn oil, olive oil, peanut oil, sunflower oil, sesame oil, nut oils, and coconut oils. Nut oils include, but are not limited to, almond oil, cashew oil, hazelnut oil, macadamia oil, mongongo nut oil, pecan oil, pine nut oil, pistachio oil, sacha inchi oil, and walnut oil. Melon and gourd seed oils are very common and inexpensive. The oils listed above include saturated, mono-unsaturated, and polyunsaturated fatty acids that are soluble in many compositions, especially the less polar or non-polar ones.

Exemplary preservatives include, for example, sorbic acid and its salts, benzoic acid and its salts, calcium propionate, sodium nitrite, sulfites (sulfur dioxide, sodium bisulfite, potassium hydrogen sulfite, etc.) and disodium ethylenediaminetetraacetic acid (EDTA). Other exemplary preservatives include ethanol and methylchloroisothiazolinone, rosemary extract, hops, salt, sugar, vinegar, alcohol, diatomaceous earth and castor oil, citric and ascorbic acids, vitamin C, and vitamin E.

Exemplary antioxidants for use with the liquid repellent include, but are not limited to, tocopherols (e.g., α-tocopherol, γ-tocopherol, etc), ascorbic acid, as well as synthetic antioxidants such as propyl gallate, tertiary butylhydroquinone, butylated hydroxytoluene (BHT), butylated hydroxyanisole (BHA), phenolic alcohols, flavonoids, catechins, related molecules thereof, and anthocyanins and their glycosides. The antioxidants can be soluble in most of the compositions and can react efficiently with oxygen, and therefore offer a way to decrease oxidation, breakdown, and polymerization of the liquid repellent compositions. In some embodiments, the oxidant can also be a preservative.

While representative carriers, preservatives, and antioxidants have been listed above, it is to be appreciated that other carriers, preservatives, and antioxidants not specifically listed above can also be used.

In use, the repellent fixture can be placed in a location where biting and stinging insect repellence is desired. For example, in some embodiments, the repellent fixture is placed in an outdoor area to repel mosquitoes and other biting and stinging insects. The outdoor areas can include, for example, patio areas such as a table, an outdoor dining area, a deck; a picnic area; a camping ground, etc. In some embodiments, the repellent fixture can be hung or otherwise affixed from tree branches, garden posts, patio/deck umbrella posts, etc., to create a spatial repellent shield around the human activity.

The following examples are provided to illustrate, not limit, the invention.

Example 1 compares the repellent release rates of slotted plastic tubes versus solid plastic tubes. Example 2 compares the liquid repellent distribution in slotted plastic tubes versus solid plastic tubes. Example 3 compares light reflection and illumination using a light emitting diode (LED) in a slotted plastic tube and in a solid plastic tube.

EXAMPLES

Example 1

Release Rate Comparison

This example has a slotted tube having 17% less surface area than an analogous solid tube having the same diameter and length. The slots can reduce the maximum repellent loading amounts and can increase the release/loading ratios. Release Rates of Mosquito Repellent from Porous Plastic Tubes With/Without Slots Release rate experiments for the repellent porous plastic tubes were conducted in a chemical ventilation hood in a laboratory at approximately 20° C. Each tube was placed onto the inside of a white cap with a diameter of 7 cm. These white caps were placed on a tray to elevate them slightly off the inside surface of the hood. Each tube was labeled on the tray for easy identification. The tubes were loaded on the balance with liquid mosquito repellent formulation from the top by a pipette to let it soak down the tube for uniform distribution. The weight of repellent was recorded. For Experiment 1, the release rates were started on Day 1. For Experiment 2, the release rates were also started on Day 1. For Experiment 3, the release rates were started on Day 7.

As shown in the Table 1, at similar or even lower repellent loading amounts, the repellent release rates from the tubes with only 6% open slot areas was 17-26%, 11-17%, and 6-13% higher than ones from the solid tubes, at $1^{st}$ hour, $1^{st}$ day and $2^{nd}$ day, respectively. The repellent release rates from the porous plastic tubes with 17.4% open slot areas at $1^{st}$ hour, $1^{st}$ day and $2^{nd}$ day were ~50%, ~34% and ~19% higher than from the solid tubes, respectively, even at lower loading amounts.

TABLE 1

Release rates of mosquito repellent from plastic tubes with or without slots.

| Exp. # | Tube type | % of slot area | Loading (g) | Release rates (g/d) | | | % of release rate increased by having the slots | | |
|---|---|---|---|---|---|---|---|---|---|
| | | | | 1st hr | 1st day | 2nd day | 1st hr | 1st day | 2nd day |
| 1 | Solid | 0.0 | 7.81 | 1.77 | 1.26 | 0.90 | 26.55 | 17.46 | 13.46 |
| | 45-slots | 6.0 | 8.00 | 2.24 | 1.48 | 1.02 | | | |

TABLE 1-continued

Release rates of mosquito repellent from plastic tubes with or without slots.

| Exp. # | Tube type | % of slot area | Loading (g) | Release rates (g/d) | | | % of release rate increased by having the slots | | |
|---|---|---|---|---|---|---|---|---|---|
| | | | | 1st hr | 1st day | 2nd day | 1st hr | 1st day | 2nd day |
| 2 | Solid | 0.0 | 7.69 | 1.74 | 1.24 | 0.88 | 16.67 | 11.29 | 5.92 |
| | 45-slots | 6.0 | 7.34 | 2.03 | 1.38 | 0.93 | | | |
| 3 | Solid | 0.0 | 7.00 | 1.44 | 1.04 | 0.75 | 50.69 | 33.65 | 18.67 |
| | 45-slots | 17.4 | 5.89 | 2.17 | 1.39 | 0.89 | | | |

The slots on the porous plastic tubes increase both the release overall rates and the release-loading ratios significantly, by creating more airflow through the tube body, and by having more uniform distribution of the repellent liquid on the slotted tube surface.

Example 2

Liquid Repellent Distribution

Without wishing to be bound by theory, it is believed that the multiple staggered slots on the tubes not only reduce the overall loading areas and increase the airflow through the tubes, but also create multiple partially separated thin disks, which can reduce the running-down effect of the repellent liquid after application to the funnel member.

An experiment was conducted to study the running-down rate of a liquid repellent on slotted tubes versus solid tubes, after application to the tubes to a top funnel member connected to the tubes. The repellent liquid ran much faster on the solid tubes than on the slotted tubes. It took on average 45 minutes for the repellent liquid reach down to the bottom edge at all directions for the solid tubes, whereas 1-1.5 hours were needed for tubes with 45 slots. Twenty-four hours after loading a repellent liquid onto the slotted and solid tubes, the slotted tube showed a more uniform distribution of the repellent liquid over the length of the tube, when compared to the solid tube. Thus, with the staggered slots, the repellent liquid would not quickly run vertically to the bottom section by gravity but would go around the staggered slots slowly; thereby more uniformly distribute the liquid distribution on the tube surface than on the solid tube, resulting in more active-releasing surface areas.

Example 3

LED Light Reflection and Illumination

An experiment was carried out to compare LED light illumination of a slotted tube vs. a solid tube. When an LED light is incorporated at the bottom of a slotted or solid tube, directing the light up through the tube, the slotted tube exhibited stronger and better light refection and illuminating effects than the solid tube.

While illustrative embodiments have been illustrated and described, it will be appreciated that various changes can be made therein without departing from the spirit and scope of the disclosure.

The invention claimed is:

1. A spatial repellent system comprising:
a fixture comprising (i) a slotted tube having a plurality of elongate slots; (ii) a peripheral tube having a plurality of apertures therethrough, wherein the peripheral tube is disposed radially outwardly from the slotted tube; (iii) a base that engages a bottom end of the slotted tube and a bottom end of the peripheral tube; and (iv) a cap assembly that engages a top end of the slotted tube and a top end of the peripheral tube, wherein the cap assembly comprises a conical portion that is configured to funnel a liquid repellant outwardly and through a port of the cap assembly onto the top end of the slotted tube, and the slotted tube is configured to adsorb the liquid repellant; and
the liquid repellent is configured to flow downwardly by gravity and to be adsorbed onto the slotted tube such that volatiles of the adsorbed liquid repellent are gradually released from the slotted tube.

2. The spatial repellent system of claim 1, wherein the slotted tube defines an axis, and the plurality of elongate slots are oriented approximately perpendicular to the axis.

3. The spatial repellent system of claim 1, wherein the cap assembly comprises a cap member and a funnel member that slidably engages the cap member, wherein the funnel member includes a wall portion that receives the top end of the slotted tube and the port configured to provide a flow path for the liquid repellent to flow through the port and onto the slotted tube.

4. The spatial repellent system of claim 1, wherein the base further comprises a light element configured to illuminate the slotted tube.

5. The spatial repellent system of claim 1, wherein the liquid repellent comprises an essential oil repellent composition.

6. The spatial repellent system of claim 5, wherein the essential oil repellent composition is selected from the group consisting of clove oil, lemongrass oil, peppermint oil, and cinnamon oil.

7. The spatial repellent system of claim 5, wherein the essential oil repellent composition is selected from the group consisting of clove oil, lemongrass oil, geranium oil, and rosemary oil.

8. The spatial repellent system of claim 5, wherein the essential oil repellent composition is selected from the group consisting of lemongrass oil, peppermint oil, geranium oil, rosemary oil, and citronella oil.

9. The spatial repellent system of claim 5, wherein the spatial repellent system is adapted to repel stinging insects, biting insects, or both the stinging and biting insects.

10. The spatial repellent system of claim 5, wherein the spatial repellent system is adapted to repel mosquitoes, paper wasps, hornets, yellow jackets, cockroaches, ants, or any combination thereof.

11. The spatial repellent system of claim 5, wherein the spatial repellent system is adapted to repel mosquitoes, paper wasps, hornets, yellow jackets, or any combination thereof.

* * * * *